United States Patent [19]

Wohltjen et al.

[11] 4,438,203

[45] Mar. 20, 1984

[54] METHOD AND APPARATUS FOR DETERMINATION OF LUBRICANT STABILITY

[75] Inventors: Henry Wohltjen, Burke, Va.; Paul J. Sniegoski; Harold Ravner, both of Bethesda, Md.

[73] Assignee: The United States of America as represented by the Secretary of the Navy, Washington, D.C.

[21] Appl. No.: 388,356

[22] Filed: Jun. 14, 1982

[51] Int. Cl.³ .................................................. G01N 33/30
[52] U.S. Cl. .................................... 436/60; 422/80; 422/94; 436/160
[58] Field of Search ......................... 436/60, 160, 139; 422/78, 80, 94, 95

[56] References Cited

U.S. PATENT DOCUMENTS

| 4,007,629 | 2/1977 | Hochstein . |
| 4,155,713 | 5/1979 | Mahoney ............................. 436/60 |
| 4,250,142 | 2/1981 | Kollmai ............................ 422/94 X |
| 4,310,487 | 1/1982 | Yamada et al. .................. 422/80 X |

FOREIGN PATENT DOCUMENTS

| 2029015 | 3/1980 | United Kingdom .................. 422/80 |
| 535337 | 1/1977 | U.S.S.R. ................................. 436/60 |

*Primary Examiner*—Arnold Turk
*Attorney, Agent, or Firm*—Robert F. Beers; William T. Ellis; Alan P. Klein

[57] ABSTRACT

Method and apparatus for determining when a lubricant has reached the end of its useful life due to oxidative degradation. The apparatus continuously monitors the evolution of gaseous emission from the lubricant when subjected to oxidizing conditions, and detects the increased gas emission accompanying oxidative breakdown.

10 Claims, 2 Drawing Figures

METHOD AND APPARATUS FOR DETERMINATION OF LUBRICANT STABILITY

BACKGROUND OF THE INVENTION

This invention relates to the testing of materials, and more particularly to the monitoring of the degradation of lubricant materials.

The evaluation of lubricant stability is very important for designers, producers, and users of lubricants. Perhaps the greatest interest is focused on evaluating the stability of lubricants in an oxidizing environment since oxidative degradation is the primary cause of lubricant failure. Typically, a lubricant sample whose volume may lie in the range of 10 to 1,000 ml) is placed in a temperature controlled oven (heated between 50° and 300° C.) and air or oxygen is bubbled through the sample at a constant flow rate. Samples are taken from the apparatus at regular intervals and analyses are performed to measure such things as viscosity change, acidity increase or peroxide formation. In most tests, an antioxidant material is added to the lubricant, and the rate at which the antioxidant disappears is measured and related to lubricant stability. A popular alternative method for oxidation testing of lubricants requires a closed "bomb" which is charged with oxygen gas and the lubricant. The rate at which the oxygen pressure drops is directly proportional to the extent of lubricant oxidation. This particular test requires elaborate apparatus and large lubricant samples. The previously mentioned techniques (i.e., viscosity, acidity, etc.) require large samples of lubricant along with periodic sampling and analysis of the test mixture (i.e., lots of manual labor). Clearly the existing techniques are inadequate if one is interested in using small sample sizes (e.g., 1 ml) or if automation of the evaluation process is desired.

SUMMARY OF THE INVENTION

It is therefore an object of the invention to monitor the degradation of lubricant materials.

Another object is to provide an easily interpreted signal when a lubricant tested under oxidizing conditions has reached the end of its useful life so that the stable lifetime of the lubricant can be determined.

These and other objects of the invention are achieved in one aspect by a method for determining the stable lifetime of a lubricant when subjected to oxidizing conditions. A sample of the lubricant under test is disposed in an oxidizing cell and the cell is heated to the oxidation temperature of the lubricant while oxygen is bubbled at a constant flow rate through the cell. The concentration of combustible gas in the oxygen flowing out of the cell is detected and the time elapsing until the onset of a rapid increase in the concentration of combustible gas is measured. The elapsed time is a measure of the stable lifetime of the lubricant when subjected to the oxidizing conditions of the test.

In another aspect, the invention involves an apparatus for determining the stable lifetime of a lubricant when subjected to oxidizing conditions. The apparatus includes an oxidation cell for containing a sample of the lubricant, means for heating the cell to the oxidation temperature of the lubricant, and means for bubbling oxygen at a constant flow rate through the cell. The apparatus further includes means for detecting the concentration of combustible gas in oxygen flowing out of the cell; and means for measuring the time elapsing until the onset of a rapid increase in the concentration of combustible gas.

The invention provides continuous monitoring of the lubricant. Sampling, with its resulting waste of time and lubricant, is eliminated. Small volumes of lubricant (e.g. less than 1 ml) are easily measured since the combustible gas-detecting means is highly sensitive. This capability is very important during the research and development phase of lubricant production when it may be expensive to provide large sample volumes of exotic experimental lubricants. The apparatus is uncomplicated, inexpensive to construct, and can easily be adapted to existing oxidation test facilities. It provides an electrical signal which lends itself easily to automation of the testing procedure. The signal provided by the apparatus has a very large signal-to-noise ratio and can be easily interpreted by unskilled operators. Further, the apparatus is rugged and reliable.

Additional advantages and features will become apparent as the subject invention becomes better understood by reference to the following detailed description when taken in conjunction with the accompanying drawings wherein:

DESCRIPTION OF THE PREFERRED EMBODIMENT

In addition to experiencing changes in viscosity or acidity a lubricant undergoing oxidation will inevitably evolve combustible gas products. It has been discovered by the inventors that the evolution of gas rapidly increases at the onset of lubricant-oxidative breakdown. The close timing of these events permits gas evolution to be used as an effective indicator of lubricant lifetime.

Figure 1:
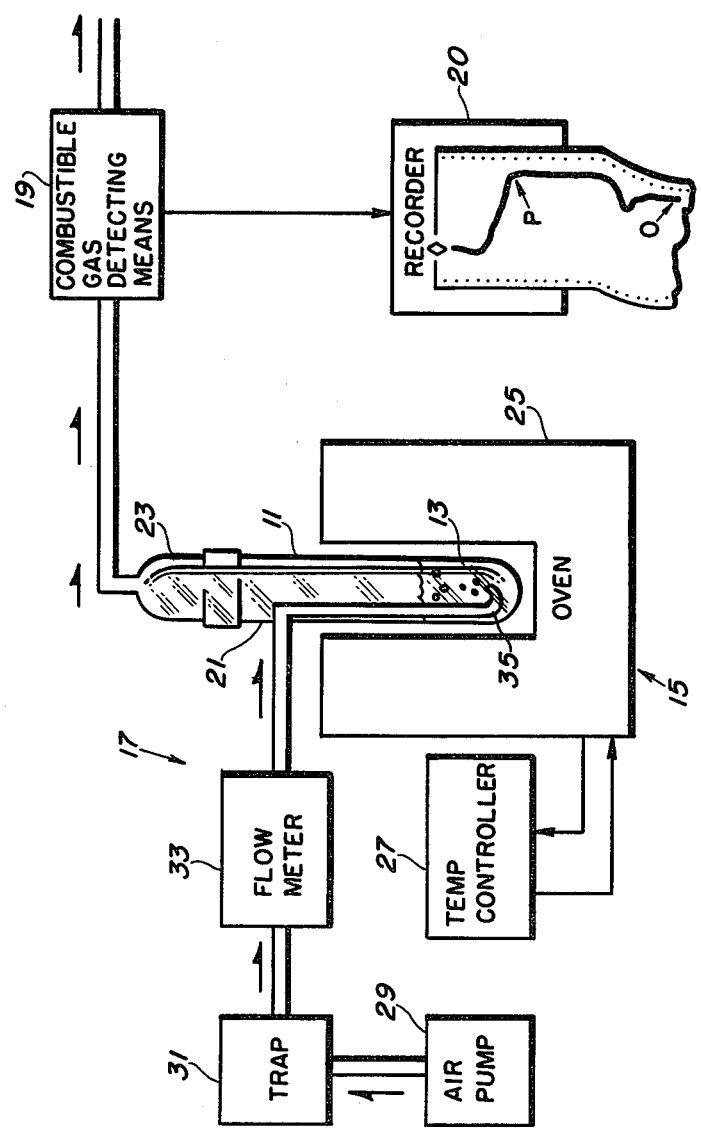
FIG. 1 is a block diagram of an embodiment of the invention.

Referring to FIG. 1, the apparatus for determining the stable lifetime of a lubricant when subjected to oxidizing conditions includes an oxidation cell 11 to contain a sample of the lubricant 13; a heating means 15 which heats the cell; a bubbling means 17 which bubbles oxygen at a constant flow rate through the cell; a detecting means 19 which detects the concentration of combustible gas in the oxygen flowing out of the cell; and a measuring means 20 which measures the time elapsing until the onset of a rapid increase in the concentration of combustible gas.

A Pyrex (TM) glass tube having an inlet 21 and a vent 23 may, for example, be employed for the oxidation cell 11. The heating means 15 may comprise, for example, an oven 25, and a controller 27 to control the oven temperature.

While the bubbling means may take a variety of forms, conveniently it may take the form illustrated in FIG. 1 of an air pump 29; a trap 31 communicating with the air pump; a flow meter 33 communicating with the trap; and a side-arm bubbler tube 35 disposed inside the cell 11 and communicating with the flow meter through the inlet 21.

The combustible gas-detecting means 19 may likewise take a variety of forms. It may, for example, take the form shown in FIG. 2 of a gas sensor 37, such as a Figaro Engineering, Osaka Japan, model TGS 813, positioned over the vent 23 of the cell 11; a summing amplifier 39 connected to the gas sensor and including means 40 for connecting the amplifier's input to an external voltage source; an inverting amplifier 41 connected to the output of the summing amplifier; and a potential divider 43 connected to the output of the investing amplifier. The measuring means 20 may comprise, for example, a chart recorder connected to the potential divider.

In operation, the oxidation cell 11 is cleaned, filled with a 1 to 2 ml. sample of the lubricant 13 to be tested, and is inserted in the oven 25 and heated to the oxidation temperature of the lubricant. The air pump 29 pumps ambient air at a constant flow rate through the trap 31 which filters moisture and other contamination from the air and passes the dry, filtered air to the flow meter 33 which measures its flow rate. The bubbler tube 35 receives the oxygen-containing air from the flow meter 33 and bubbles it through the sample 13 of the lubricant and out of the cell 11 and over the gas sensor 37 contained in the combustible gas detecting means 19.

Figure 2:
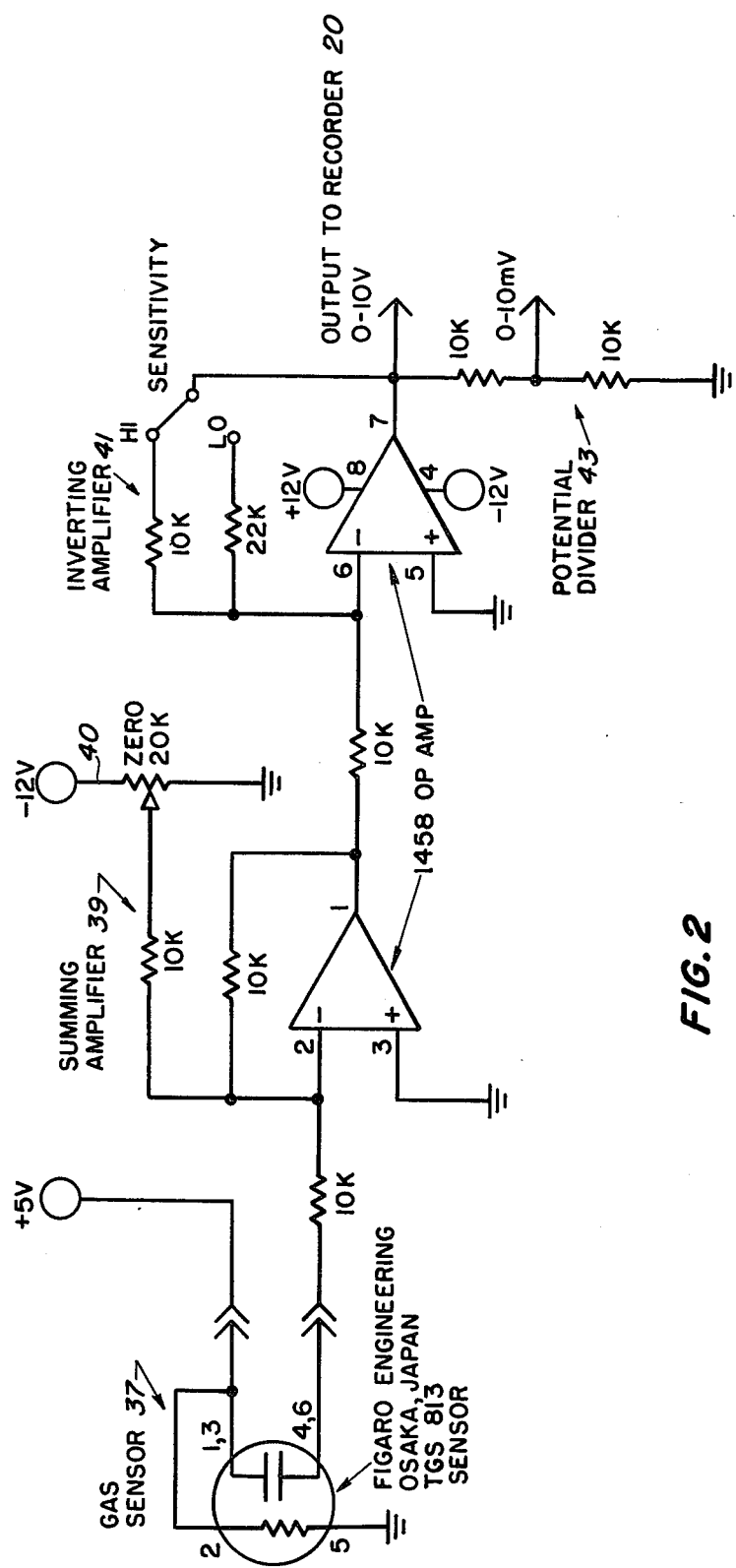
FIG. 2 is a detailed circuit diagram of an embodiment of the combustible gas detecting means of FIG. 1.

Referring to FIG. 2 the gas sensor 37 responds to the presence of combustible gas in the oxygen-containing air flowing out of the cell 11 by generating a sensing signal. The signal from the sensor 37 is amplified in the inverting amplifier 41, suitably scaled down by the potential divider 43, and applied to the chart recorder 20 (FIG. 1) which records it as a function of time. The summing amplifier 39 is provided to balance out the quiescent signal from the sensor 37 when no combustible gas is present in the oxygen-containing air flowing out of the cell 11.

The onset of oxidative breakdown of the sample 13 of the lubricant is marked by a rapid increase in the concentration of combustible gas in the oxygen-containing air flowing out of the cell 11 and is accompanied by the generation of a correspondingly high recorded signal on the chart recorder 20. The stable lifetime of the lubricant when subjected to the oxidizing conditions of the test can be determined by measuring the elapsed time from the beginning of the oxidation test (point O on the chart of recorder 20 in FIG. 1) to the onset of the large recorded signal shift (point P on the chart of recorder 20 in FIG. 1). The elapsed time is the distance along the chart feed axis between points O and P, multiplied by the chart feed rate.

Obviously, many modifications and variations of the present invention are possible in light of the above teachings. For example, instead of the semiconductor gas sensor shown in FIG. 2, a sensor using infrared light transmission through the exhaust gas stream, or a sensor using the flow of ionization current through the exhaust gas stream, may be used for gas sensor 37. The chart recorder may be replaced by a panel meter and a clock, or by a computer. The use of a computer makes it possible to monitor many sensors simultaneously. It is therefore to be understood that within the scope of the appended claims, the invention may be practiced otherwise than as specifically described.

What is claimed as new and desired to be secured by Letters Patent of the United States is:

1. An apparatus for determining the stable lifetime of a lubricant when subjected to oxidizing conditions, comprising:
   an oxidation cell for containing a sample of the lubricant;
   means for heating the cell to the oxidation temperature of the lubricant;
   means for bubbling oxygen at a constant flow rate through the cell;
   means for detecting the concentration of combustible gas in oxygen flowing out of the cell; and
   means for measuring the time elapsing until the onset of a rapid increase in the concentration of combustible gas.

2. The apparatus recited in claim 1 wherein the heating means includes:
   an oven; and
   a temperature-controller for the oven.

3. The apparatus recited in claim 1 wherein the bubbling means includes:
   a pump for pumping ambient air;
   a trap communicating with the pump for filtering moisture and other contamination from the air;
   a flow meter communicating with the trap for measuring the flow rate of the pumped air; and
   a side-arm bubbler tube disposed inside the oxidation cell and communicating with the flow meter for receiving the air and bubbling it through the lubricant sample and out of the cell.

4. The apparatus recited in claim 1 wherein the combustible gas-detecting means includes:
   a gas sensor positioned over the cell in the path of the oxygen flowing out of the cell and responsive to the presence of combustible gas in the oxygen for generating a sensing signal;
   an inverting amplifier for amplifying the signal from the sensor,
   a potential divider connected to the output of the inverting amplifier for scaling down the amplified signal; and
   a summing amplifier connected between the gas sensor and the inverting amplifier and including means for connecting an input of the summing amplifier to an external voltage source to balance out a quiescent signal from the sensor when no combustible gas is present in the oxygen flowing out of the cell.

5. The apparatus recited in claim 4 wherein the measuring means includes:
   a chart recorder connected to the potential divider for recording the scaled-down signal as a function of time.

6. A method for determining the stable lifetime of a lubricant when subjected to oxidizing conditions comprising the steps of:
   disposing a sample of the lubricant under test in an oxidation cell;
   heating the cell to the oxidation temperature of the lubricant;
   bubbling oxygen at a constant flow rate through the cell;
   detecting the concentration of combustible gas in the oxygen flowing out of the cell; and
   measuring the time elapsing until the onset of a rapid increase in the concentration of combustible gas.

7. The method recited in claim 6 wherein the bubbling step includes:
   pumping ambient air;
   filtering moisture and other contamination from the air;
   measuring the flow rate of the pumped air; and
   transferring the air to a bubbler tube inside the cell.

8. The method recited in claim 6 wherein the heating step includes:
   inserting the cell in an oven; and
   controlling the temperature of the oven.

9. The method recited in claim 6 wherein the detecting step includes:

positioning a gas sensor over the cell in the path of the oxygen flowing out of the cell;

amplifying the signal from the sensor;

scaling down the amplified signal; and balancing out a quiescent signal from the sensor when no combustible gas is present in the oxygen flowing out of the cell.

10. The method recited in claim 9 wherein the measuring step includes:

recording the scaled-down signal as a function of time.

* * * * *